(12) United States Patent
Faries, Jr. et al.

(10) Patent No.: US 8,148,666 B2
(45) Date of Patent: Apr. 3, 2012

(54) METHOD AND APPARATUS FOR PROTECTING STERILE DRAPES IN SURGICAL THERMAL TREATMENT SYSTEMS

(75) Inventors: Durward I. Faries, Jr., Las Vegas, NV (US); Bruce R. Heymann, Vienna, VA (US); David Hendrix, Ashburn, VA (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 586 days.

(21) Appl. No.: 11/514,310

(22) Filed: Sep. 1, 2006

(65) Prior Publication Data

US 2007/0089753 A1 Apr. 26, 2007

Related U.S. Application Data

(60) Provisional application No. 60/712,906, filed on Sep. 1, 2005.

(51) Int. Cl.
*A61B 19/00* (2006.01)
*A61F 7/00* (2006.01)
*F27D 11/00* (2006.01)

(52) U.S. Cl. ........ 219/429; 219/430; 219/433; 219/439; 604/114

(58) Field of Classification Search .................. None
See application file for complete search history.

(56) References Cited

U.S. PATENT DOCUMENTS

| 2,174,425 A * | 9/1939 | Schlumbohm | 220/573.1 |
| 2,323,356 A * | 7/1943 | Rosay | 220/574.3 |
| 2,599,192 A | 6/1952 | Miller | |
| 2,613,511 A | 10/1952 | Walsh | |
| 2,807,701 A | 9/1957 | Conlin et al. | |
| 2,813,450 A | 11/1957 | Dzus | |
| 3,249,070 A | 5/1966 | Day et al. | |
| 3,519,979 A | 7/1970 | Bodenstein | |
| 3,869,596 A | 3/1975 | Howie | |
| 3,902,484 A | 9/1975 | Winters | |
| 4,053,954 A | 10/1977 | Chapman | |
| 4,242,932 A | 1/1981 | Barmore | |
| 4,270,067 A | 5/1981 | Thomas et al. | |
| 4,284,880 A | 8/1981 | Keiser | |
| 4,393,659 A | 7/1983 | Keyes et al. | |
| 4,458,139 A | 7/1984 | McClean | |
| 4,474,016 A | 10/1984 | Winchell | |

(Continued)

FOREIGN PATENT DOCUMENTS

JP 61-185967 11/1986

(Continued)

*Primary Examiner* — Joseph M Pelham
(74) *Attorney, Agent, or Firm* — Edell, Shapiro & Finnan, LLC

(57) ABSTRACT

Surgical drapes employed with thermal treatment systems are re-enforced according to the present invention. This protects against punctures and tears when objects are placed in a receptacle formed by a drape within a thermal treatment system basin to contain a sterile medium. In one embodiment, a plate or pad is used to protect the drape. The plate or pad may be formed of rigid or flexible material of various configurations. The plate or pad may be solid or perforated (e.g., with holes, slots, mesh, etc.), and may be loosely placed on or fixedly attached to the drape. The plate or pad may have depending feet or protrusions that support the plate spaced above the drape material. Alternatively, the drape may be utilized without the plate and include a thick intermediate section resistant to puncture that is disposed within the thermal treatment system basin.

55 Claims, 10 Drawing Sheets

U.S. PATENT DOCUMENTS

| | | |
|---|---|---|
| 4,522,041 A | 6/1985 | Menzel |
| 4,569,259 A | 2/1986 | Rubin et al. |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,953,269 A | 9/1990 | Ragsdale |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,351,675 A | 10/1994 | Brodsky |
| 5,363,746 A | 11/1994 | Gordon |
| 5,374,813 A | 12/1994 | Shipp |
| 5,383,476 A | 1/1995 | Peimer et al. |
| 5,386,835 A | 2/1995 | Elphick et al. |
| 5,396,905 A | 3/1995 | Newman et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,443,322 A | 8/1995 | Jozat et al. |
| 5,457,962 A | 10/1995 | Faries, Jr. et al. |
| 5,463,213 A | 10/1995 | Honda |
| 5,480,302 A | 1/1996 | Fife |
| 5,502,980 A | 4/1996 | Faries, Jr. et al. |
| 5,517,170 A | 5/1996 | Peters |
| 5,522,095 A | 6/1996 | Faries, Jr. et al. |
| 5,522,805 A | 6/1996 | Vancaillie et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,549,543 A | 8/1996 | Kim |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,666,831 A | 9/1997 | Doros |
| 5,715,547 A | 2/1998 | Becker et al. |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,913,650 A | 6/1999 | Daoud |
| 5,950,438 A | 9/1999 | Faries, Jr. et al. |
| D417,809 S | 12/1999 | Hofman |
| 6,003,328 A | 12/1999 | Faries, Jr. et al. |
| 6,035,855 A | 3/2000 | Faries, Jr. et al. |
| 6,077,267 A | 6/2000 | Huene |
| 6,087,636 A | 7/2000 | Faries, Jr. et al. |
| 6,091,058 A | 7/2000 | Faries, Jr. et al. |
| 6,102,044 A | 8/2000 | Naidyhorski |
| D441,996 S | 5/2001 | Wright |
| 6,231,596 B1 | 5/2001 | Collins |
| 6,255,627 B1 | 7/2001 | Faries, Jr. et al. |
| 6,259,067 B1 | 7/2001 | Faries, Jr. et al. |
| D447,900 S | 9/2001 | Wright |
| 6,341,704 B1 | 1/2002 | Michel, Jr. |
| 6,371,121 B1 | 4/2002 | Faries, Jr. et al. |
| 6,448,571 B1 | 9/2002 | Goldstein |
| 6,586,950 B1 | 7/2003 | Sargent et al. |
| 6,593,552 B1 | 7/2003 | Li |
| 6,701,174 B1 | 3/2004 | Krause et al. |
| 6,810,881 B2 | 11/2004 | Faries, Jr. et al. |
| 6,860,271 B2 | 3/2005 | Faries, Jr. et al. |
| 6,884,970 B2 | 4/2005 | Lehman |
| 6,910,485 B2 | 6/2005 | Faries, Jr. et al. |
| 6,918,395 B2 | 7/2005 | Faries, Jr. et al. |
| 6,927,365 B2 | 8/2005 | Li |
| 7,041,941 B2 | 5/2006 | Faries, Jr. et al. |
| 7,128,275 B2 | 10/2006 | Kammer et al. |
| 7,176,030 B2 | 2/2007 | Faries, Jr. et al. |
| D546,943 S | 7/2007 | Kammer et al. |
| D546,944 S | 7/2007 | Kammer et al. |
| D547,444 S | 7/2007 | Kammer et al. |
| 7,276,675 B2 | 10/2007 | Faries, Jr. et al. |
| 7,307,245 B2 | 12/2007 | Faries, Jr. et al. |
| 7,309,472 B2 | 12/2007 | Michaelson et al. |
| 7,311,660 B2 | 12/2007 | Gomez |
| 7,347,210 B2 | 3/2008 | Faries, Jr. et al. |
| 7,350,373 B1 | 4/2008 | Faries, Jr. et al. |
| D568,989 S | 5/2008 | Kammer et al. |
| D569,970 S | 5/2008 | Kammer et al. |
| 7,417,205 B2 | 8/2008 | Faries, Jr. et al. |
| 7,418,966 B2 | 9/2008 | Faries, Jr. et al. |
| 7,441,714 B2 | 10/2008 | Kammer et al. |
| 7,459,657 B2 | 12/2008 | Kammer et al. |
| 7,560,667 B2 | 7/2009 | Kammer et al. |
| 7,671,302 B1 | 3/2010 | Faries, Jr. |
| 7,728,262 B1 | 6/2010 | Faries, Jr. |
| 7,854,230 B2 | 12/2010 | Faries, Jr. et al. |
| 7,854,387 B2 | 12/2010 | Kammer et al. |
| 7,874,167 B2 | 1/2011 | Kammer et al. |
| 7,903,957 B2 | 3/2011 | Kammer et al. |
| 7,959,860 B2 | 6/2011 | Faries, Jr. et al. |
| 2003/0132216 A1 | 7/2003 | Li |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2005/0247169 A1 | 11/2005 | Faries, Jr. et al. |
| 2006/0065276 A1 | 3/2006 | Kammer et al. |
| 2006/0086361 A1 | 4/2006 | Kammer et al. |
| 2006/0091128 A1 | 5/2006 | Kammer et al. |
| 2006/0091129 A1 | 5/2006 | Colonna |
| 2006/0194324 A1 | 8/2006 | Faries, Jr. et al. |
| 2006/0260443 A1 | 11/2006 | Faries, Jr. et al. |
| 2006/0289016 A1 | 12/2006 | Kammer et al. |
| 2006/0289445 A1 | 12/2006 | Colonna |
| 2007/0084936 A1 | 4/2007 | Kammer et al. |
| 2007/0089753 A1 | 4/2007 | Faries, Jr. et al. |
| 2008/0152937 A1 | 6/2008 | Kammer et al. |
| 2008/0272199 A1 | 11/2008 | Kammer et al. |
| 2009/0014547 A1 | 1/2009 | Kammer et al. |
| 2009/0112057 A1 | 4/2009 | Kammer et al. |
| 2009/0255540 A1 | 10/2009 | Faries, Jr. |
| 2009/0301107 A1 | 12/2009 | Kammer et al. |
| 2010/0116810 A1 | 5/2010 | Faries, Jr. |
| 2010/0200561 A1 | 8/2010 | Faries, Jr. |
| 2011/0270367 A1 | 11/2011 | Faries, Jr. et al. |

FOREIGN PATENT DOCUMENTS

| | | |
|---|---|---|
| JP | 06-123532 | 5/1994 |

\* cited by examiner

METHOD AND APPARATUS FOR PROTECTING STERILE DRAPES IN SURGICAL THERMAL TREATMENT SYSTEMS

CROSS-REFERENCE TO RELATED APPLICATIONS

This application claims priority from U.S. Provisional Patent Application Ser. No. 60/712,906, entitled "Method and Apparatus For Protecting Sterile Drapes in Surgical Warming Systems" and filed Sep. 1, 2005, the disclosure of which is incorporated herein by reference in its entirety.

BACKGROUND OF THE INVENTION

1. Technical Field

The present invention pertains to improvements in methods and apparatus for thermally treating surgically sterile liquid, and in using these types of systems, typically located in a surgical operating room, to thermally treat objects (e.g., sponges, needles, scalpels, endoscopes, containers, etc.) in a sterile manner. In particular, the present invention is an improvement of the methods and apparatus disclosed in U.S. Pat. No. 4,393,659 (Keyes et al.), U.S. Pat. No. 4,934,152 (Templeton), U.S. Pat. No. 5,333,326 (Faries, Jr. et al.), U.S. Pat. No. 5,522,095 (Faries, Jr. et al.), U.S. Pat. No. 6,087,636 (Faries, Jr. et al.) and U.S. Pat. No. 6,810,881 (Faries, Jr. et al.), the disclosures of which are incorporated herein by reference in their entireties.

2. Discussion of Related Art

The Keyes et al. patent discloses a surgical slush producing system having a cabinet with a heat transfer basin at its top surface. A refrigeration mechanism in the cabinet takes the form of a closed refrigeration loop including: an evaporator in heat exchange relation to the exterior of the heat transfer basin; a compressor; a condenser; and a refrigeration expansion control, all located within the cabinet. A separate product basin is configured to be removably received in the heat transfer basin. Spacers, in the form of short cylindrical stubs or buttons are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile sheet of material, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency in the product basin.

As noted in the Templeton patent, the above-described system has a number of disadvantages. In particular, the separate product basin must be removed and resterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterilized drape impervious to the sterile surgical liquid, the drape being made to conform to the basin and directly receive the sterile liquid. Congealed liquid is scraped off the sides of the conformed drape receptacle to form the desired slush.

In addition, the Templeton patent discloses an electrical heater disposed at the bottom of the basin to convert the sterile slush to warmed liquid, or heat additional sterile liquid added to the basin. The Templeton patent describes the need for such warm sterile liquid as occurring after a surgical procedure is completed to facilitate raising the body cavity of a surgery patient back to its normal temperature by contact with the warm liquid. However, there are a number of instances during a surgical procedure when it is desirable to have simultaneous access to both the sterile warm liquid and the sterile surgical slush. For example, if the surgical slush is not of the desired consistency (e.g., too thick), the availability of warm sterile liquid to be added to the slush permits rapid adjustability of the slush consistency. Likewise, maintaining instruments at or near body temperature during surgery is a desirable feature permitted by warm sterile liquid. Of course, if the warm sterile liquid is simultaneously available with the surgical slush, there is no need to wait for the slush to melt at the end of the surgical procedure. Finally, the simultaneous provision of slush and warm liquid permits the two to be comprised of different compounds as is sometimes necessary for various surgical procedures.

In response to the foregoing problems, the Faries, Jr. et al. patent (U.S. Pat. No. 5,333,326) provides a thermal treatment system having a basin for containing warm surgical liquid placed adjacent a surgical slush basin of the type, for example, disclosed in the Templeton patent. The warming basin may be a separate unit secured to the pre-existing surgical slush unit, or may be constructed as part of an integral cabinet for the warming and cooling basins. A large surgical drape covers both of the basins and contains the warm liquid and the slush in a sterile manner. Alternatively, the thermal treatment system may include only the warming basin utilizing a drape to cover the basin and contain warm surgical liquid in a sterile manner.

Thus, the warmer disclosed in the aforementioned Faries, Jr. et al. patent utilizes a basin for containing thermally treated sterile liquids (e.g., irrigation solutions, etc.). Since the basin itself is generally not sterile, and to avoid contaminating objects that are placed in the basin during a surgical procedure, a sterile surgical drape is placed in the basin to line or cover the bottom and side walls of the basin and serves as a barrier to contain the thermally treated liquid isolated from the non-sterile basin walls. A warming type basin may be a separate unit, or the basin may be constructed as part of an integral cabinet for both warming and cooling (i.e., surgical slush) basins, or the warming basin may be separate but secured to a pre-existing surgical slush unit.

Generally, users of the aforementioned Faries, Jr. et al. system utilize the liquid in the warming basin to heat objects (e.g., medical instruments, containers) placed in the basin. However, during the course of a surgical procedure, objects are often tossed, dropped or not carefully placed in the basin which sometimes causes the surgical drape or sheet to be punctured or torn, thereby compromising the required sterility. Often it is not until after the surgical procedure has been completed that it becomes evident that sterility has been compromised. Although some open basin thermal treatment systems and drapes employ a trivet or stand (e.g., U.S. Pat. No. 6,087,636) to elevate objects within the basin above the basin floor, or have been adapted to detect when the cover has been punctured and alert the surgical staff (e.g., U.S. Pat. No. 6,810,881), these systems generally do not shield or reinforce the drape to prevent puncture.

OBJECTS AND SUMMARY OF THE INVENTION

Accordingly, it is an object of the present invention to prevent puncturing of a surgical drape disposed in a thermal treatment system basin when objects (e.g., medical instruments, containers, etc.) are placed in the basin.

It is another object of the present invention to prevent puncturing of a surgical drape disposed in a thermal treatment system basin by covering or reinforcing the drape container floor.

Yet another object of the present invention is to prevent puncturing of a surgical drape disposed in a thermal treatment system basin by covering the drape container floor with a plate or pad to protect the drape.

A further object of the present invention is to prevent puncturing of a surgical drape disposed in a thermal treatment system basin by employing a thick intermediate drape section disposed within the basin to protect the drape.

The aforesaid objects may be achieved individually and/or in combination, and it is not intended that the present invention be construed as requiring two or more of the objects to be combined unless expressly required by the claims attached hereto.

According to the present invention, reinforcement is provided for surgical drapes employed with thermal treatment systems to protect the drapes against punctures and tears during use. This can be accomplished in several ways. For example, in one embodiment a plate or pad is used to protect the drape. The plate or pad may be formed of rigid or flexible material of various configurations. The plate or pad may be solid or perforated (e.g., with holes, slots, mesh, etc.), and may be loosely placed on or fixedly attached to the drape. The plate or pad may have depending feet or protrusions that support the plate spaced above the drape material. The configurations may be combined to provide a device that protects against punctures while still allowing for sterile thermal treatment of the contained liquid and the objects placed in the thermal treatment system basin. Alternatively, the drape may be utilized without the plate and include a thick intermediate section resistant to puncture that is disposed within the thermal treatment system basin.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
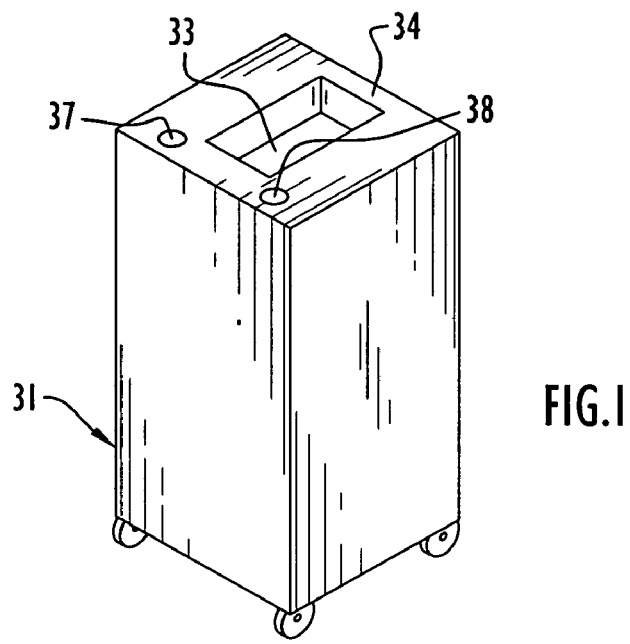
FIG. 1 is a view in perspective of an exemplary thermal treatment system containing a substantially rectangular warming basin employed by the present invention.

Referring to FIG. 1 of the accompanying drawings, a typical thermal treatment system for thermally treating a sterile medium (i.e., liquid) employed by the present invention includes a cabinet or housing 31 and a warming basin 33 recessed into the top surface 34 of cabinet 31. Basin 33 may be any shape, however, by way of example only, the basin is illustrated as being substantially rectangular. A heater power switch 37 and a temperature controller/indicator 38 are provided on top surface 34 adjacent the warming basin. It is to be understood that the thermal treatment system described above may have various configurations and include a plurality of basins warming and/or cooling a sterile medium. An example of such a system is disclosed in the aforementioned Faries, Jr. et al. (U.S. Pat. No. 5,333,326) patent.

Figure 2:
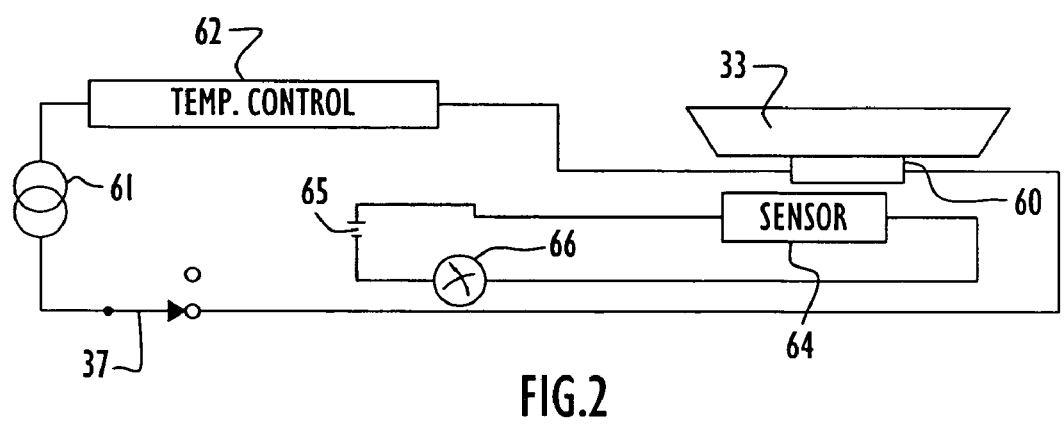
FIG. 2 is an electrical schematic diagram of the heating unit employed in the thermal treatment system of FIG. 1.

The manner of heating sterile liquid in warming basin 33 is illustrated schematically in FIG. 2. Specifically, an electrical circuit includes a power source 61 connected in series with a temperature control unit 62, a heater element or pad 60, and power control switch 37. Heater 60 is typically a thin wafer-like member disposed along the bottom surface of heating basin 33, secured to the basin by a suitable pressure sensitive adhesive having efficient heat transfer characteristics. Heater 60 has smaller dimensions than the basin bottom and is disposed at the approximate center of the bottom surface of the basin. The heater, for example, may be of the type described in the aforementioned Templeton patent. Temperature control unit 62 includes a device for adjusting current passing through the heating element 60 so as to permit selective adjustment of the heat applied to the liquid in basin 33. The power switch 37 permits selective application and removal of current flow with respect to heater 60.

A temperature sensor 64 is disposed adjacent basin 33 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicator 38 described above. For examples of the operation of the heating unit, reference is made to the Faries, Jr. et al. (U.S. Pat. No. 5,333,326) and other above-mentioned patents.

A sterile drape suitable for covering the top surface of the system described above is made of a material that is impervious to the heated liquid, and is sufficiently soft and flexible to conform to the walls of basin 33 and form a drape receptacle. The thickness of the drape is preferably minimized to render thermal transfer therethrough most efficient, yet the thickness is sufficient to resist tearing and puncturing of the drape during normal use. Typically, by way of example only, a drape is made of materials commonly used in hospitals for surgical drapes and has a thickness in the range of 4.5 to 6.0 mils. The drape may also be made of polyurethane film as disclosed for the drape in the aforementioned Templeton patent. The drape may further include a preformed container portion contoured to match the contour of a basin. The preformed container portion is typically thicker than the remaining portions of the drape described above in order to resist puncture and enable the container portion to maintain the shape of the basin. By way of example only, the container portion may be made of a heavy gauge polyethylene/ionomer resin blend having a thickness of approximately ten through sixteen mils. The percentage of ionomer resin in the blend is in the approximate range of forty to seventy percent. The drape is designed to be disposable after a single use and is provided presterilized and prepackaged in a leak-proof plastic bag or other sealed container to preserve the sterile nature of the drape during storage.

The drape is typically placed over the system and covers the top surface and hangs down the sides of the system cabinet while a portion of the drape is pushed down into, and conforms to, the basin to form a drape receptacle for containing heated liquid. Generally, objects (e.g., medical instruments, containers, etc.) may be warmed in the basin by placing the objects in heated liquid contained by the drape receptacle. However, during the course of a surgical procedure, objects are often tossed, dropped or not carefully placed in the basin which sometimes causes the surgical drape or sheet to be punctured or torn, thereby compromising the required sterility. Often it is not until after the surgical procedure has been completed that it becomes evident that sterility has been compromised.

Figure 3:
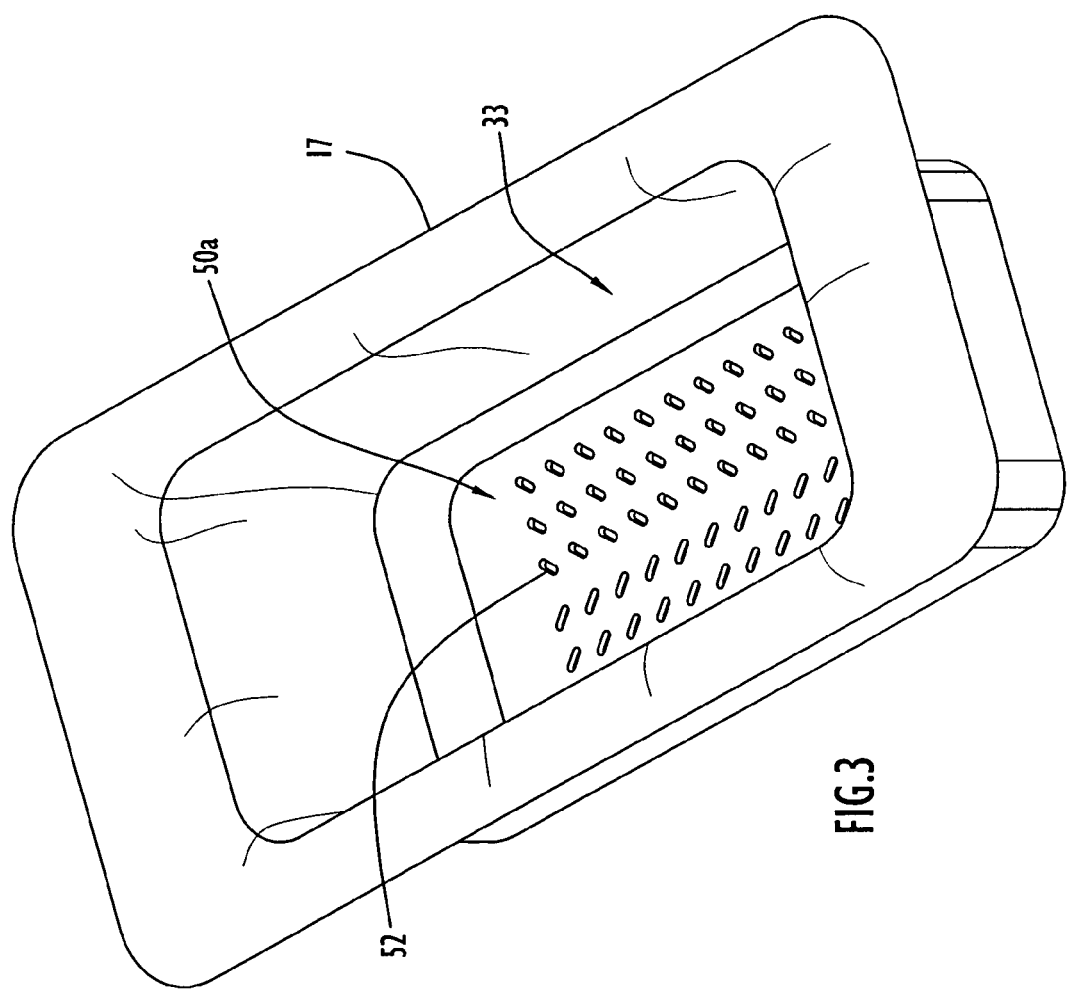
FIG. 3 is a view in perspective of the drape and plate according to the present invention disposed within the basin of the thermal treatment system of FIG. 1.
Figure 4:
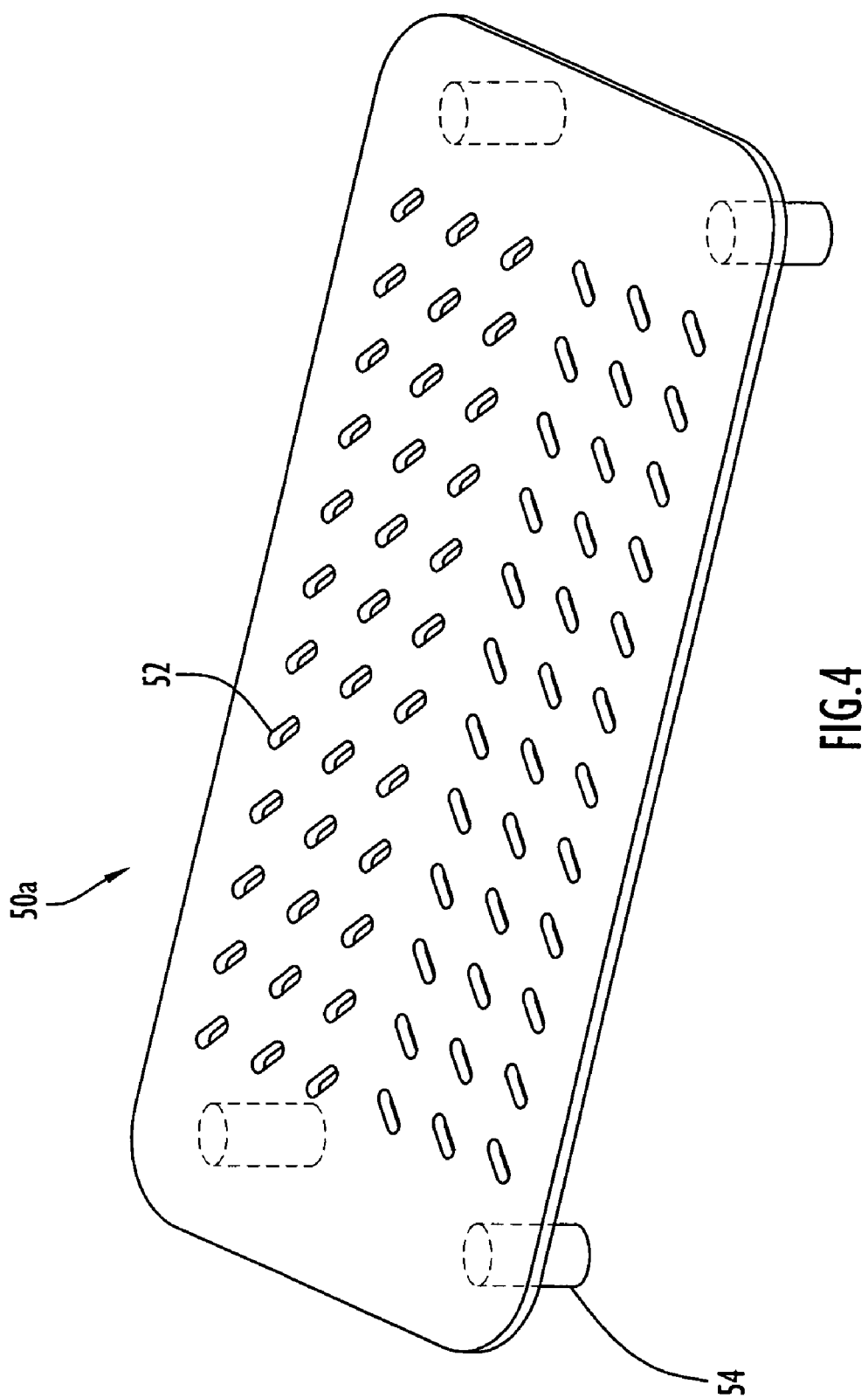
FIG. 4 is a view in perspective of the drape plate of FIG. 3 further including feet.

Accordingly, the present invention is directed toward reinforcing the drape to protect against punctures and tears during use, thereby preserving sterility during a medical procedure. A plate or pad for protecting the drape against puncture is illustrated in FIGS. 3-4. Specifically, a plate or pad 50a is substantially rectangular and disposed on the drape within the drape container formed in the thermal treatment system basin. The plate includes plural through holes 52 defined therein to allow for flow of the thermally treated liquid through the plate or pad to permit circulation of the contained liquid and assure uniform thermal treatment of objects disposed in the basin. By way of example, the holes are arranged in six generally parallel rows extending in a longitudinal direction, where a set of three longitudinal rows is disposed on each of a respective longitudinal half of the plate. The holes preferably extend through the plate or pad at an angle other than vertical (e.g., at an angle other than perpendicular to the top surface of the plate) and are angled away from the center of the basin. The angled orientation of the holes prevents the ends of sharp instruments that are thrown into the basin from passing entirely through a hole in the plate or pad and penetrating the drape while still allowing uniform heating of the contained liquid. However, the holes may be oriented in any suitable direction.

Plate or pad 50a is preferably in the form of a flexible plastic or rubber mat having a thickness generally on the order of at least one quarter of an inch and approximate transverse (e.g., width) and longitudinal (e.g., length) dimensions of four and eight inches, respectively. If the plate or pad material is sufficiently puncture-resistant in thinner configurations, a lesser thickness may be used. For applications where flexibility is not required, the plate may be constructed of a more rigid plastic, urethane or metal material. The plate material and thickness must not be capable of puncture by a needle or other sharp-ended object tossed, dropped or carelessly placed into the basin during a surgical procedure. The plate is preferably sized to cover the entire bottom portion of the basin and in some cases, where required, may be configured to extend up along one or more sides of the basin. Since plate or pad 50a is intended to be disposable after each surgical procedure, the material, thickness, length and width are selected to minimize cost without compromising the function of protecting the drape against puncture from an object that is carelessly placed, dropped or tossed into the basin. Plate or pad 50a in this embodiment is not merely a second sheet or layer of the same material and thickness as the drape being protected since such a sheet or layer would not, in most instances, provide the required protection against puncture by a sharp object.

Depending on the nature of the surgical procedure and the need for sharp instruments, plate or pad 50a can either be selectively placed on top of the drape before a surgical procedure, or the plate may be supplied by the manufacturer permanently attached to the drape. The permanent attachment may be effected in a variety of ways (e.g., applying standard biocompatible adhesives, RF welding, ultrasonic welding, double-sided tape, heat sealing, etc.). Preferably, the periphery of plate or pad 50a is continuous with a configuration that substantially matches the periphery of the bottom wall of the basin. For example, in the case where the basin bottom wall is rectangular (FIG. 1), plate or pad 50a is likewise rectangular and matches the basin bottom wall to substantially cover that wall. It will be appreciated that this feature, although desirable, is not necessarily limiting on the scope of the invention since the plate or pad can be configured to cover more or less than the entire bottom wall of the basin. Likewise, the basin need not be rectangular and the pad or plate, if intended to match the basin bottom, can be configured accordingly.

Plate or pad 50a may further be provided with a plurality of depending feet or protrusions 54 (FIG. 4) extending from the plate bottom surface to define a space between the drape portion lining the bottom wall of the basin and the bottom surface of the plate or pad. Each foot 54 is preferably disposed toward a respective corner of plate 50a; however, the feet may be disposed at any suitable locations. The space between the drape and plate bottom surface allows for circulation of the warmed contained liquid and for even heating of the liquid and objects in the basin.

Figure 5:
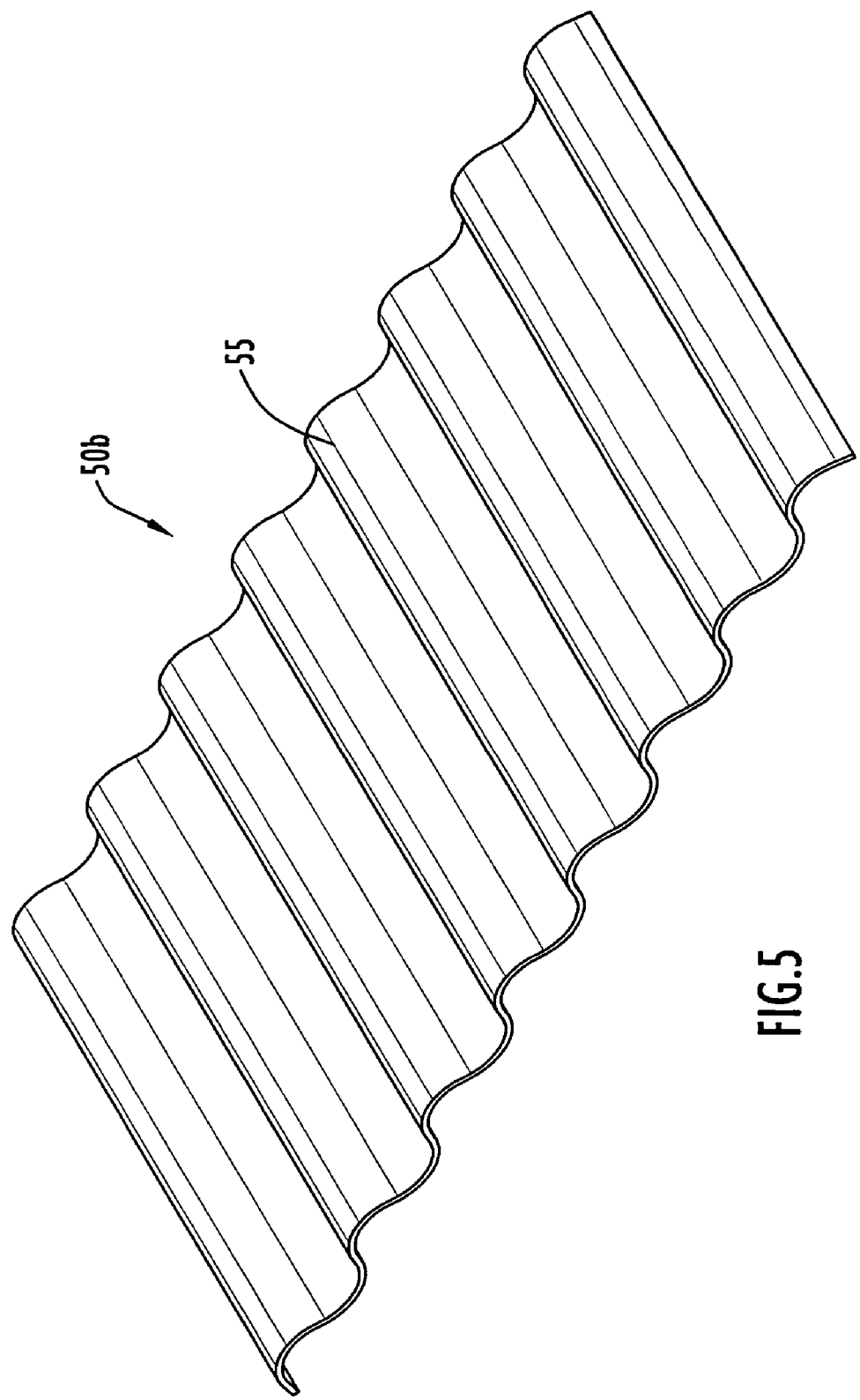
FIG. 5 is a view in perspective of an alternative embodiment of the drape plate including a corrugated surface according to the present invention.

Alternatively, the plate or pad need not be flat on the plate top and bottom surfaces. For example, the plate may be corrugated (e.g., similar to a washboard) with or without the through holes described above as illustrated in FIG. 5. In particular, plate 50b is substantially similar to plate 50a described above and includes a series of corrugations 55 to provide undulating top and bottom plate surfaces. By way of example, the corrugations are defined in a transverse direction in the plate surfaces with successive corrugations extending longitudinally across the plate. However, the corrugations may be of any quantity (or frequency), size or shape and may be disposed at any locations and arranged in any fashion (e.g., defined and/or extend successively in transverse or longitudinal directions, etc.).

Figure 6:
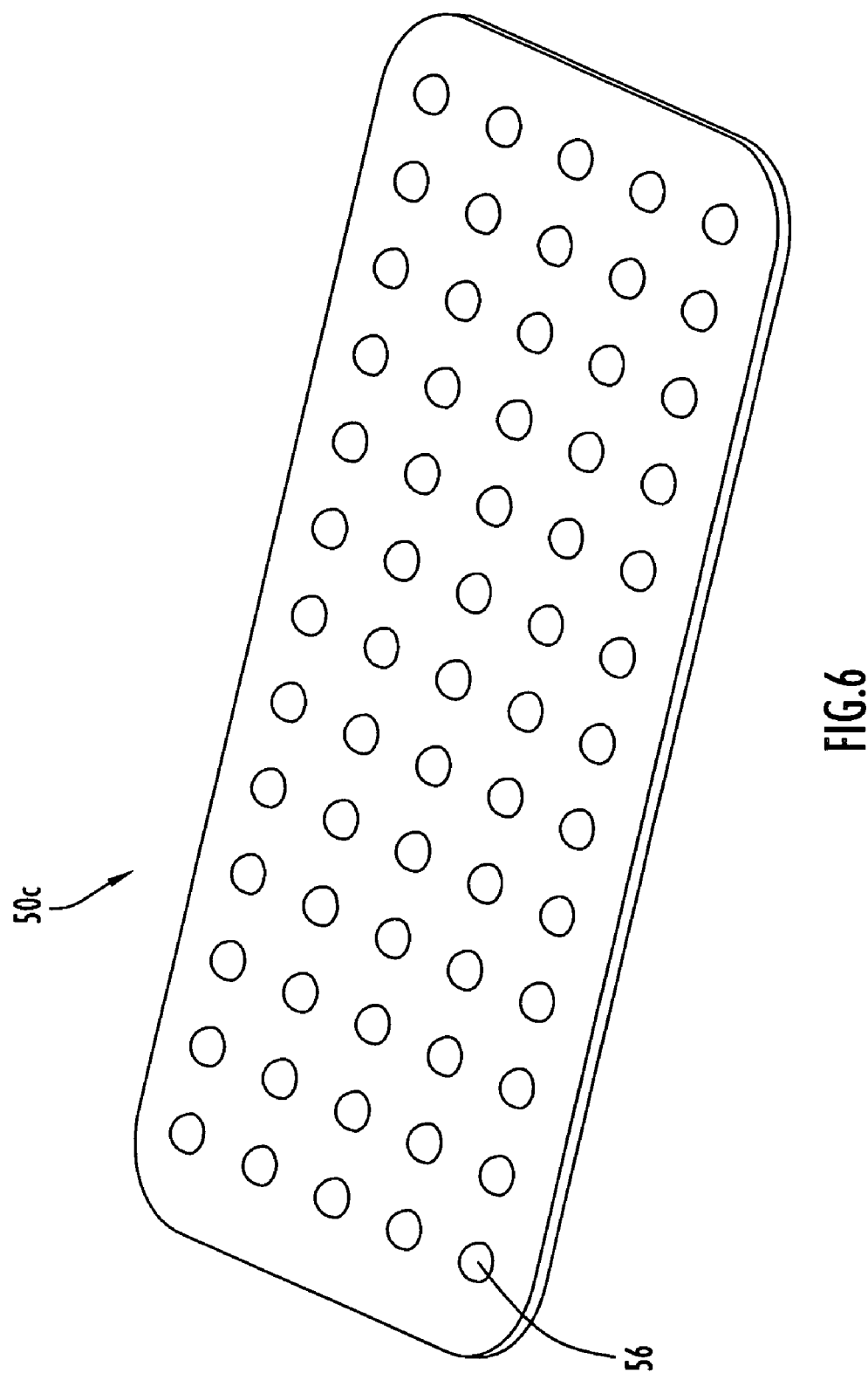
FIG. 6 is a view in perspective of the drape plate including a surface with relatively small convex protrusions according to the present invention.

Further, the top and/or bottom surfaces of the plate may be provided with regularly or irregularly spaced small convex protrusions as illustrated in FIG. 6. In particular, plate 50c is substantially similar to plate 50a described above and includes a series of small convex or dome-like protrusions 56 disposed on the plate top surface to assist in absorption of impact of an object placed in the basin. Protrusions 56 may be of any quantity, size or shape and may be disposed on the plate at any locations (e.g., any locations on the top and/or bottom plate surfaces, etc.) and arranged in any fashion. By way of example, the protrusions are arranged in five generally parallel rows extending in a longitudinal direction, where protrusions 56 include diameters in the approximate range of one-third to one-half inch.

Figure 7:
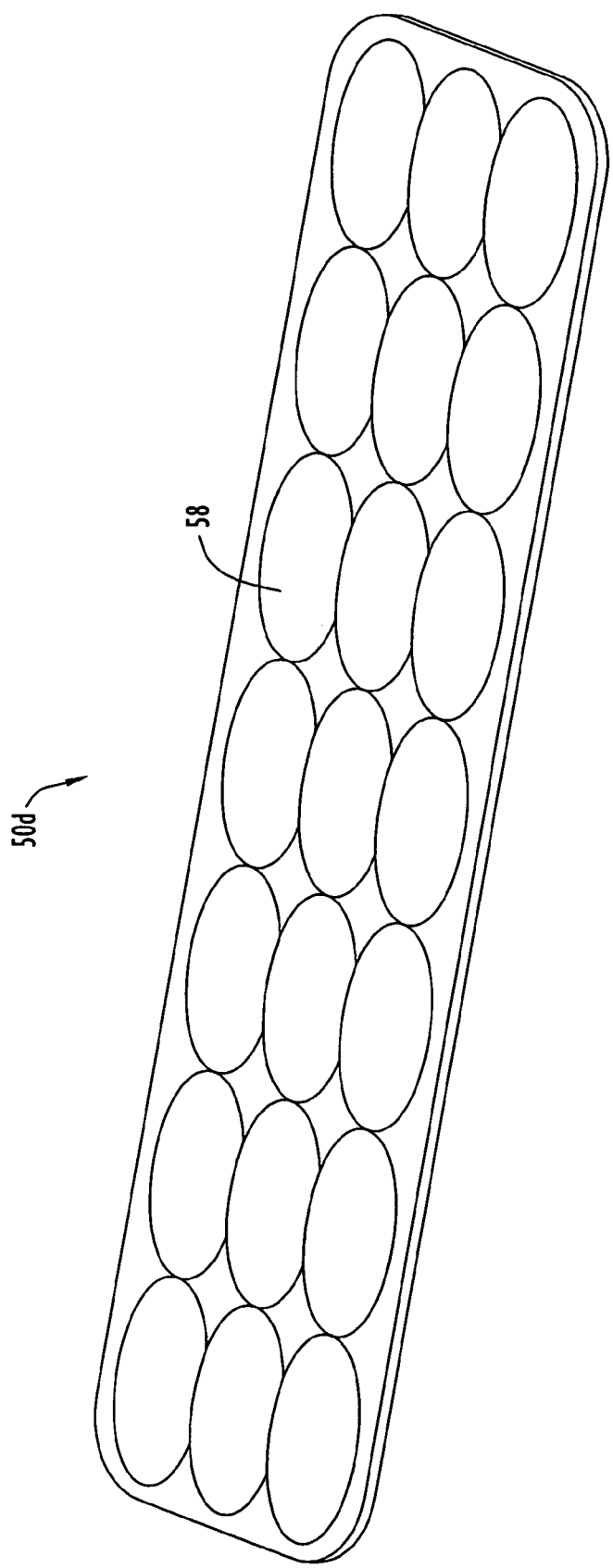
FIG. 7 is a view in perspective of the drape plate including a surface with relatively large convex protrusions according to the present invention.

Moreover, the plate may include one or more relatively large convex protrusions disposed on the plate top surface as illustrated in FIG. 7. In particular, plate 50d is substantially similar to plate 50a described above and includes a series of large convex protrusions 58 disposed on the plate top surface. Protrusions 58 include dimensions greater than those of protrusions 56 and are preferably located to dominate the plate top surface area sufficiently to receive the impact of any object tossed or placed into the basin. Protrusions 58 absorb the impact of the sharp object at a location spaced further from the basin bottom than the remainder of the top surface of the plate or pad. Protrusions 58 are preferably dome-like or pyramid-like to enable the object, after impacting the protrusion, to fall harmlessly to the bottom of the basin. The protrusions may be of any quantity, size or shape and may be disposed on the plate at any locations (e.g., any locations on the top and/or bottom plate surfaces, etc.) and arranged in any fashion. By way of example, protrusions 58 are arranged in three generally parallel rows extending in a longitudinal direction, where protrusions 58 include diameters in the approximate range of one to one and one-third inches.

Figure 8:
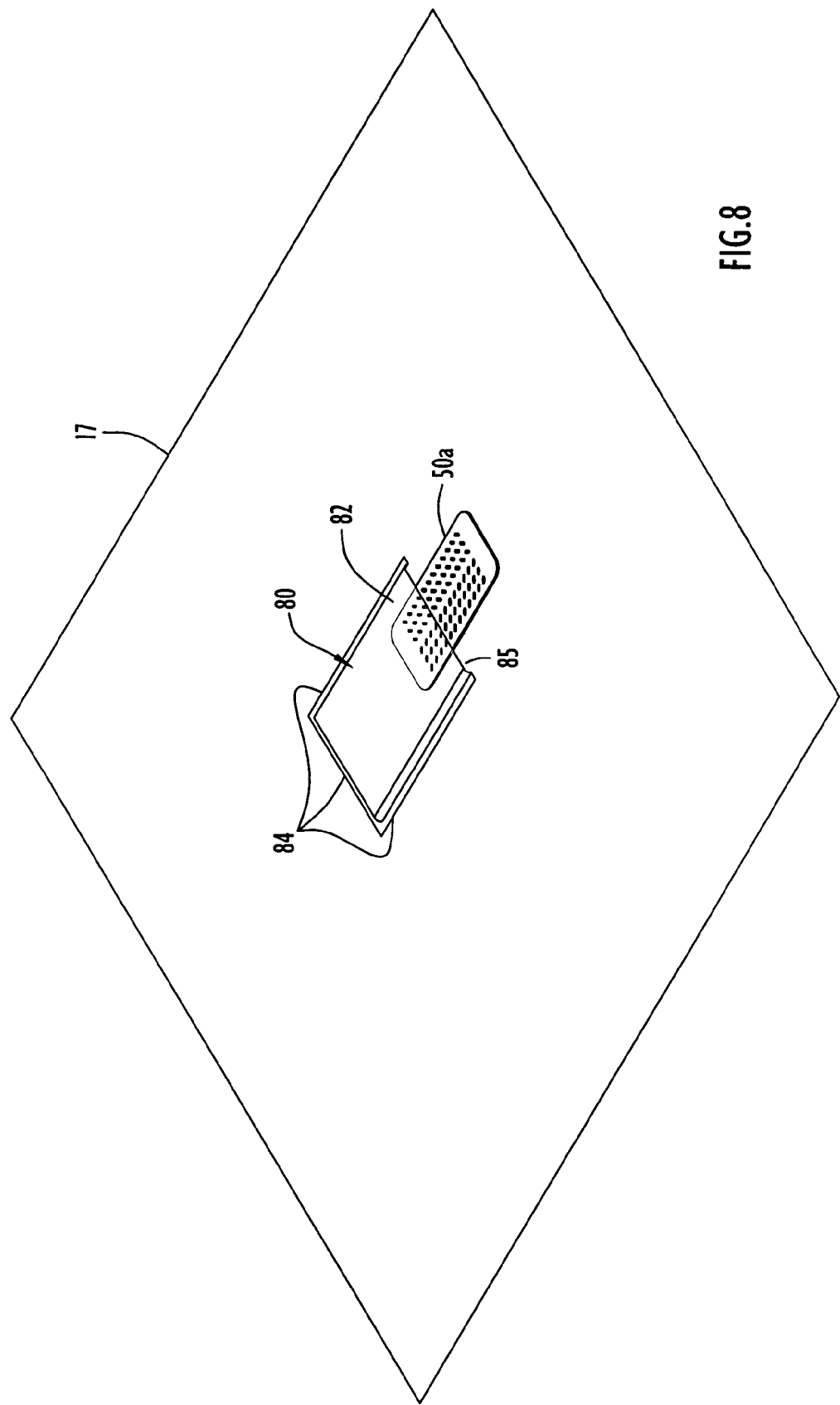
FIG. 8 is a view in perspective of an alternative drape with a pouch to secure the plate to the drape according to the present invention.

Drape 17 may further include a pouch to receive a plate as illustrated in FIG. 8. In particular, drape 17 includes a pouch 80 disposed on a portion of the drape placed within the thermal treatment basin. The pouch is substantially rectangular and includes dimensions sufficient to contain a plate. Pouch 80 is preferably formed by a substantially rectangular material segment 82 having three segment edge portions 84 (e.g., two longitudinal edge portions and a transverse edge portion) affixed to the drape sterile surface. The remaining non-adhered segment edge portion (e.g., transverse edge portion) 85 forms an opening for insertion of the plate. By way of example only, plate 50a is illustrated as being placed within pouch 80; however, the pouch may be configured to receive any of the plates described above. Material segment 82 may include openings to enable liquid within the basin to flow through the pouch for uniform heating. The material segment is typically constructed of materials similar to those forming drape 17 described above and may be affixed to the drape via any conventional or other techniques (e.g., adhesives, welding, etc.).

Figure 9:
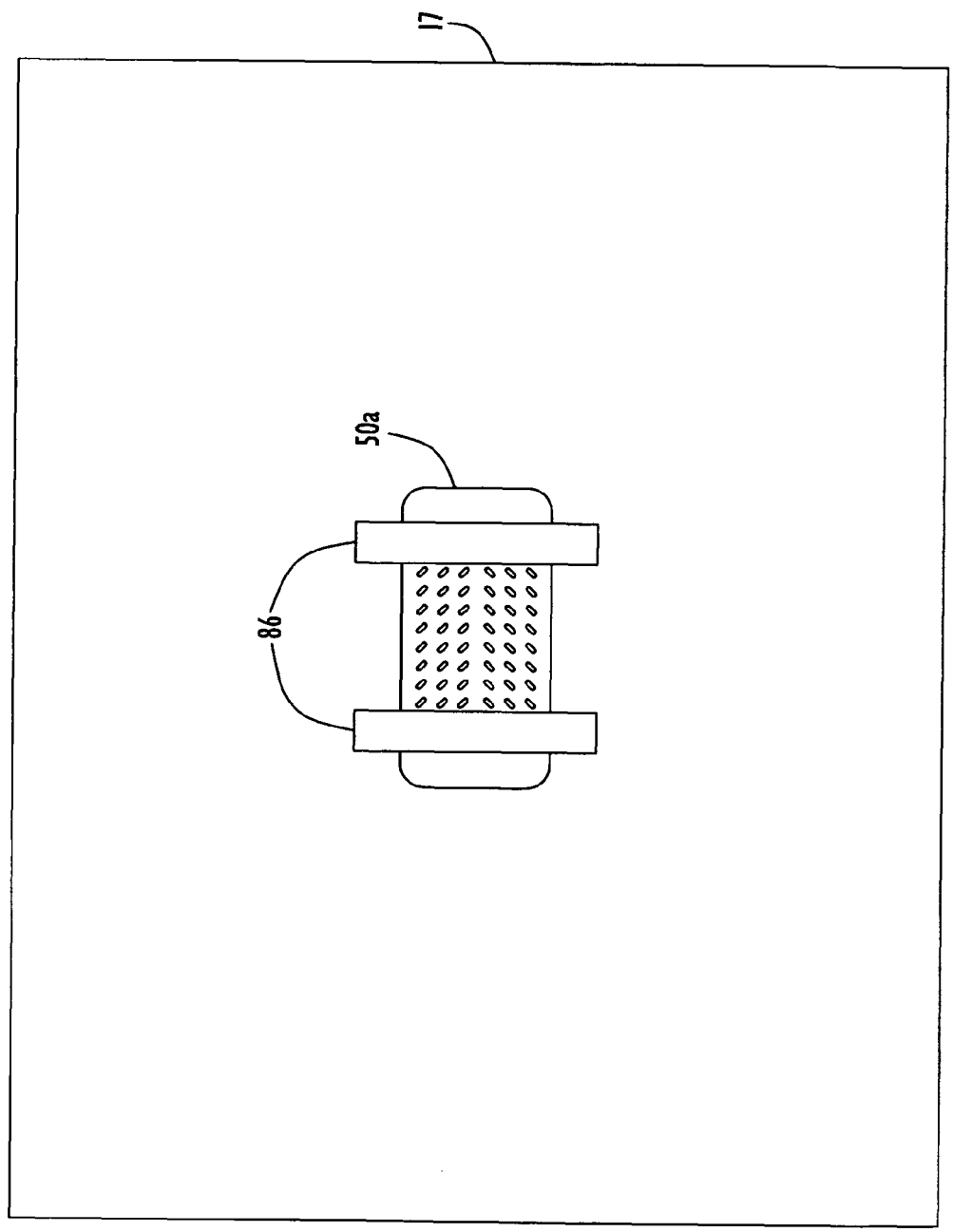
FIG. 9 is a view in perspective of a drape with fasteners to secure the plate to the drape according to the present invention.

Alternatively, drape 17 may include fasteners to secure the plate to the drape as illustrated in FIG. 9. In particular, drape 17 may include straps or ties 86 disposed on the drape portion placed in the basin to secure the plate. By way of example only, plate 50a is illustrated as being secured by straps 86; however, the straps may secure any of the plates described above to the drape. The straps or ties may be of any quantity, shape or size and may be disposed at any suitable locations on the drape to secure plate 50a thereto. The straps or ties may be constructed of any suitable materials (e.g., drape material, string or lace, etc.) and may be affixed to the drape via any conventional or other techniques (e.g., adhesives, welding, etc.). Straps 86 may be used individually or in combination with pouch 80 to secure the plate to the drape.

Figure 10:
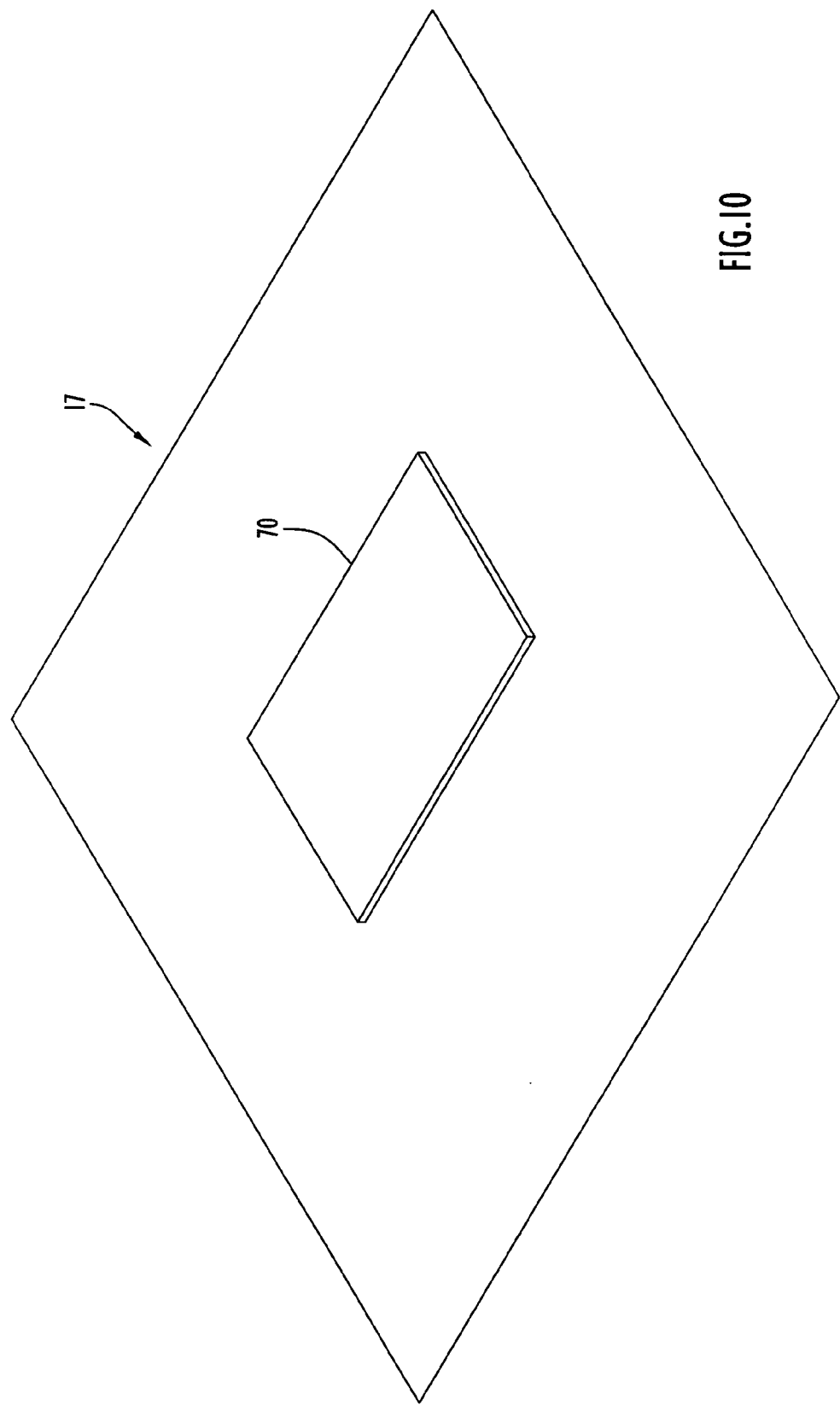
FIG. 10 is a view in perspective of a drape including a thick intermediate section to prevent puncture of the drape in accordance with the present invention.

The drape may alternatively include a thick intermediate section and be utilized without a plate as illustrated in FIG. 10. Specifically, drape 17 is constructed with a section 70 that is thicker in the area that lines the basin bottom and/or side walls to protect against punctures. The thicker section is constructed and configured to prevent penetrations of the drape without reducing drape flexibility. Section 70 is typically constructed of materials similar to those forming drape 17 (or the preformed container portion) described above and generally includes thicker dimensions than those of the preformed container portion (e.g., on the order of approximately twenty mils).

Figure 11:
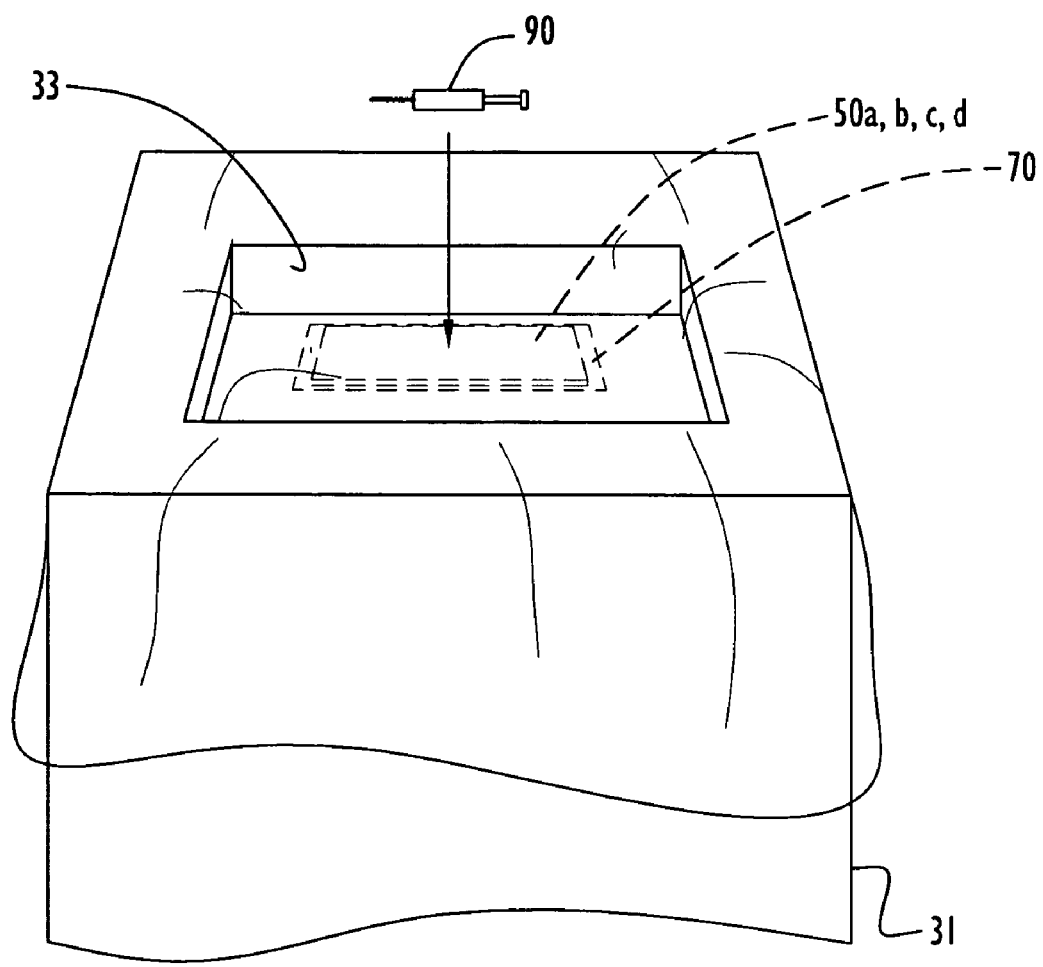
FIG. 11 is an exploded view of a medical instrument placed on a drape disposed within a basin of the thermal treatment system according to the present invention.

Operation of the drape and/or plate when disposed in a thermal treatment system basin containing heated liquid is described with reference to FIG. 11. Specifically, drape 17 is disposed over cabinet 31 and within basin 33 to form a drape receptacle as described above. A plate 50a, 50b, 50c, 50d is disposed at the basin floor either as part of the drape, or as a separate unit disposed in the basin above the drape (e.g., via pouch 80 or straps 86, unsecured to the drape, etc.). A syringe 90 and/or other sharp objects are disposed in basin 33 on the top surface of the plate, whereby the plate prevents the syringe from puncturing the drape in substantially the same manner described above for the respective plate embodiments. Alternatively, drape 17 may include thick intermediate portion 70 (FIG. 10) disposed within basin 33 to prevent puncture of the drape by syringe 90 as described above.

It will be appreciated that the embodiments described above and illustrated in the drawings represent only a few of the many ways of implementing a method and apparatus for protecting sterile drapes in surgical thermal treatment systems.

The plate or pad may be constructed of any suitable materials (e.g., flexible or rigid plastic, urethane, metal, etc.) capable of withstanding temperatures of at least one hundred sixty degrees Fahrenheit and of sufficient strength to prevent drape puncture by blunt or sharp objects (e.g., medical instruments, etc.) placed in the basin. The plate or pad may be of any quantity, size or shape, and may be constructed of any suitable materials. Preferably, the plate or pad shape is capable of fitting within and/or formed to the shape of the basin. The plate or pad may cover any portion of the basin or drape container. The plate or pad may be disposed on any part of the drape capable of being disposed in the basin and may be attached to the drape via any conventional or other techniques (e.g., ultrasonic energy, heat welding, solvents, adhesives, RF welding techniques, etc.). The plate and drape may be formed as an integral unit or, alternatively, the plate or pad may be constructed as a unit separate from the drape and secured to or placed on (e.g., in an unsecured fashion) the drape for use. The plate or pad may be implemented by any suitable shielding device capable of preventing drape puncture.

The plate or pad may include any quantity of legs or other elevation mechanisms to distance the plate or pad from the basin floor. The legs may be of any quantity, shape or size and may be disposed or attached to any portions of the plate. The entire plate or pad may be molded as a single piece to minimize cost of manufacture.

The holes in the plate or pad may be of any quantity, size or shape and may be arranged in any fashion capable of preventing drape puncture (e.g., any quantity of rows or columns oriented in any fashion with any quantity of holes in each row or column, any distribution pattern of holes, etc.). For example, the holes may be oriented at any desired angle to prevent an object from traversing the hole to contact and/or puncture the drape (e.g., angles in the approximate range between 0° and 90° relative to the plate or pad top surface). The plate or pad may alternatively be implemented without the holes. The holes may be utilized with any of the above described plate embodiments (e.g., convex portions, corrugations, etc.).

The corrugations may be of any quantity (or frequency), size or shape, may be disposed at any locations (e.g., top and/or bottom plate surfaces, etc.) and arranged in any fashion (e.g., defined and/or extend successively in transverse or longitudinal directions, etc.). The corrugations may be utilized in combination with any of the above described plate embodiments (e.g., convex protrusions, holes, etc.).

The small and large convex protrusions may be of any quantity, size or shape (e.g., dome, pyramid, etc.), may be placed at any suitable locations (e.g., top and/or bottom plate surfaces, etc.) and may be arranged in any fashion (e.g., any quantity of rows or columns oriented in any fashion with any quantity of convex protrusions in each row or column, any distribution pattern of the protrusions, etc.). The protrusions may be utilized in combination with any of the above described plate embodiments (e.g., corrugations, holes, etc.).

The drape employed with the thermal treatment system may be of any size or shape, and may be constructed of any suitable materials. The drape is preferably transparent or translucent to facilitate manipulation of controls through the drape, however, the drape may have any degree of transparency (e.g., including opaque). The drape may be manipulated in any fashion with any portions of the drape serving as a drape receptacle within a corresponding basin. The drape may be of sufficient size to accommodate and form drape receptacles within any quantity of thermal treatment system basins.

The pouch may be of any quantity, shape or size and may be disposed at any locations on the drape to receive and secure a plate. The material segment may be of any quantity, shape or size and may be attached to the drape via any conventional techniques to form the pouch. The straps or ties may be of any quantity, shape or size and may be disposed at any locations on the drape to secure a plate. The drape may alternatively include any conventional or other fastening mechanisms to secure the plate to the drape (e.g., adhesives, hook and loop fasteners, snaps, clips, etc.).

The thick intermediate section of the drape may include any suitable thickness to prevent puncture of the drape by an object (e.g., medical instrument, etc.), may be constructed of any suitable materials, and may be disposed at any drape locations. The drape with the thick intermediate section may further be employed with the plate attached to or placed on the drape to prevent drape puncture as described above.

The principles of the present invention are not limited to thermal treatment systems including a warming basin, but are equally applicable to any thermal treatment system thermally treating (e.g., heating and/or cooling) a medium. The present invention is further applicable to thermal treatment systems including a plurality of basins with each basin either warming or cooling a sterile liquid. Specifically, a thermal treatment system may include a plurality of basins disposed on a top surface for either cooling or warming a sterile liquid. The plates and drapes of the present invention may be disposed in the basins in substantially the same manner as described above. The plates and drapes prevent drape puncture as described above. Alternatively, drapes for a plural basin system may include a plurality of plates or thick intermediate sections disposed on the drape corresponding to the approximate centers of basins thermally treating the liquid. The plates or thick intermediate sections may further function as indicators designating which portions of the drape are to be disposed in the basins. The drape is disposed over the plural basin system such that portions of the drape are disposed in all basins to form drape receptacles with the plates or thick sections disposed within the basins. The plates or thick sections prevent puncture of the drape as described above.

The present invention may be utilized with any types of medical (e.g., medical instruments, containers, etc.) or other objects with any degree of sharpness (e.g., ranging from blunt to sharp, etc.) placed in the basin (or in or on any other drape portions) to prevent puncture of the drape. Further, the present invention may be utilized with any type of receptacle utilized in the basin to contain a sterile medium (e.g., receptacle formed by a drape, receptacle formed by a liner, a container, a cover, etc.) in substantially the same manner described above, while the plate or pad may be implemented by any suitable shielding device or protective member (e.g., plate, shield, pad, cover, etc.) capable of preventing puncture of the receptacle. Moreover, any portion of the top and/or bottom surfaces of the protective member may include various configurations (e.g., convex protrusions, non-flat or undulated, corrugated, etc.).

From the foregoing description, it will be appreciated that the invention makes available a novel method and apparatus for protecting sterile drapes in surgical thermal treatment systems, wherein reinforcement is provided for surgical drapes employed with thermal treatment systems to protect the drapes against punctures and tears during use.

Having described preferred embodiments of a new and improved method and apparatus for protecting sterile drapes in surgical thermal treatment systems, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An apparatus to protect a receptacle used to contain a sterile medium in a basin of a thermal treatment system, wherein an object disposed in said basin is thermally treated by said sterile medium, said apparatus comprising:
   a basin of a thermal treatment system
   a receptacle to contain said sterile medium within said basin; and
   a protective member disposed on said receptacle, wherein:
      said protective member includes a bottom surface that faces said basin and a top surface that faces away from said basin, and
      said protective member prevents said object from contacting said receptacle when said object is placed within said receptacle,
      said protective member possesses a solid, imperforate structure, and
      at least a portion of said protective member top surface includes an undulating configuration, a corrugated configuration, or a series of protrusions.

2. The apparatus of claim 1, wherein said protective member includes one of a plate, a pad and a shield of sufficient thickness and puncture resistance to prevent said object disposed in said basin from penetrating through said protective member and puncturing said receptacle.

3. The apparatus of claim 1, wherein said protective member includes a plurality of feet depending from said protective member bottom surface to space said protective member from said receptacle and to enable said sterile medium to flow between said protective member and said receptacle.

4. The apparatus of claim 1, wherein said protective member is flexible.

5. The apparatus of claim 1, wherein said protective member includes a continuous periphery contoured to substantially match and fit along a periphery of at least one of a bottom wall of said basin and a side wall of said basin.

6. The apparatus of claim 1, wherein said protective member is removably placed on said receptacle.

7. The apparatus of claim 1, wherein said receptacle includes a pouch to receive and secure said protective member to said receptacle.

8. The apparatus of claim 1, wherein said receptacle includes at least one fastener to secure said protective member to said receptacle.

9. The apparatus of claim 1, wherein said protective member is integrally formed with said receptacle.

10. The apparatus of claim 1, wherein said receptacle includes one of a container, a drape, a liner and a cover to contain said sterile medium, and wherein said drape, liner and cover are for placement within, and conform to, said basin to form said receptacle.

11. The apparatus of claim 1, wherein said thermal treatment system includes a plurality of basins to thermally treat said sterile medium and a plurality of said receptacles each disposed within a corresponding basin to contain said sterile medium within that basin, and said apparatus further includes a plurality of said protective members disposed on said receptacle within each basin and including materials resistive to penetration by said object placed in that basin to prevent puncture of said receptacle.

12. The apparatus of claim 1, wherein the bottom surface of said protective member is in direct contact with said receptacle.

13. The apparatus of claim 1, wherein:
said basin comprises:
a bottom surface and a top, receptacle-facing surface,
a heated portion directly heated by a heater disposed adjacent said basin bottom surface, and
a non-heated portion coincident with said heated portion falling outside a perimeter of said basin heater;
said receptacle contacts the heated and non-heated portions of said basin; and
at least a portion of said protective member contacts an area of said receptacle in contact with said basin heated portion.

14. The apparatus of claim 1, wherein said protective member is disposed directly onto said receptacle such that no space exists between said receptacle and said protective member bottom surface.

15. In a thermal treatment system including a basin to thermally treat a sterile medium contained therein and a receptacle being disposed within said basin to contain said sterile medium, wherein an object disposed in said basin is thermally treated by said sterile medium, a protective device disposed within said basin to protect said receptacle, said protective device comprising:
a protective member disposed on said receptacle, wherein:
said protective member includes a bottom surface that faces said basin and a top surface that faces away from said basin;
said protective member prevents said object from contacting said receptacle when said object is placed within said receptacle,
said protective member possesses a solid, imperforate structure; and
at least a portion of said protective member top surface includes an undulating configuration, a corrugated configuration, or a series of protrusions.

16. The device of claim 15, wherein said protective member includes one of a plate, a pad and a shield of sufficient thickness and puncture resistance to prevent said object disposed in said basin from penetrating through said protective member and puncturing said receptacle.

17. The device of claim 15, wherein said protective member includes a plurality of feet depending from said protective member bottom surface to space said protective member from said receptacle and to enable said sterile medium to flow between said protective member and said receptacle.

18. The device of claim 15, wherein said protective member includes a continuous periphery contoured to substantially match and fit along a periphery of at least one of a bottom wall of said basin and a side wall of said basin.

19. The apparatus of claim 15, wherein the entire bottom surface of said protective member is in direct contact with said receptacle.

20. The device of claim 15, wherein:
said basin comprises:
a bottom surface and a top, receptacle-facing surface,
a heated portion directly heated by a heater disposed adjacent said basin bottom surface, and
a non-heated portion coincident with said heated portion falling outside a perimeter of said basin heater;
said receptacle contacts the heated and non-heated portions of said basin; and
at least a portion of said protective member contacts an area of said receptacle in contact with said basin heated portion.

21. A method of preventing puncture of a receptacle used to contain a sterile medium in a basin of a thermal treatment system, wherein an object disposed in said basin is thermally treated by said sterile medium, said method comprising:
(a) re-enforcing at least a portion of said receptacle within said basin to be resistive to penetration with a protective member disposed on said receptacle, wherein:
said protective member includes a bottom surface that faces said basin and a top surface that faces away from said basin;
said protective member prevents said object from contacting said receptacle when said object is placed within said receptacle; and
said protective member possesses a solid, imperforate structure; and
at least a portion of said protective member top surface includes an undulating configuration, a corrugated configuration, or a series of protrusions.

22. The method of claim 21, wherein said protective member includes one of a plate, a pad and a shield of sufficient thickness and puncture resistance to prevent said object disposed in said basin from penetrating through said protective member and puncturing said receptacle.

23. The method of claim 21, wherein step (a) further includes:
(a.1) displacing said protective member from a receptacle floor and enabling said sterile medium to flow between said protective member and said floor via a plurality of feet depending from said protective member.

24. The method of claim 21, wherein said protective member includes a continuous periphery contoured to substantially match and fit along a periphery of at least one of a bottom wall of said basin and a side wall of said basin.

25. The method of claim 21, wherein step (a) further includes:
(a.1) removably placing said protective member on said receptacle.

26. The method of claim 21, wherein step (a) further includes:
(a.1) securing said protective member to said receptacle via a pouch disposed on said receptacle.

27. The method of claim 21, wherein step (a) further includes:
(a.1) securing said protective member to said receptacle via at least one fastener disposed on said receptacle.

28. The method of claim 21, wherein said protective member is integrally formed with said receptacle.

29. The method of claim 21, wherein said receptacle includes one of a container, a drape, a liner and a cover to contain said sterile medium, and wherein said drape, liner and cover are for placement within, and conform to, said basin to form said receptacle.

30. The method of claim 21, wherein said thermal treatment system includes a plurality of basins to thermally treat said sterile medium and a plurality of receptacles each disposed within a corresponding basin to contain said sterile medium within that basin, and wherein step (a) further includes:
(a.1) re-enforcing at least a portion of said receptacle within each said basin to be resistive to penetration by said object placed in that basin to prevent puncture of said receptacle.

31. The method of claim 21 further comprising (a.2) positioning said protective member on said receptacle such that the entire bottom surface of said protective member is in direct contact with said receptacle.

32. The method of claim 21, wherein:
said basin comprises:
a bottom surface and a top, receptacle-facing surface,
a heated portion directly heated by a heater disposed adjacent said basin bottom surface, and
a non-heated portion coincident with said heated portion falling outside a perimeter of said basin heater;
said receptacle contacts the heated and non-heated portions of said basin; and
the method further comprises (a.2) positioning at least a portion of said protective member on said receptacle such that said protective member bottom surface contacts an area of said receptacle in contact with said basin heated portion.

33. The method of claim 21 further comprising (a.2) disposing said protective member directly onto said receptacle such that no space exists between said receptacle and said protective member bottom surface.

34. An apparatus to protect a receptacle used to contain a sterile medium in a basin of a thermal treatment system, wherein an object disposed in said basin is thermally treated by said sterile medium, said apparatus comprising:
a basin of a thermal treatment system
a receptacle to contain said sterile medium within said basin; and
a protective member disposed on said receptacle, said protective member comprising:
a bottom surface that faces said basin and a top surface and that faces away from said basin, and
a plurality of holes defined therein, said plurality of holes permitting said sterile medium to flow through said protective member and thermally treat said object, wherein each hole of said plurality of holes extends from said top surface to said bottom surface, and wherein each hole of said plurality extends through the protective member at a non-perpendicular angle relative to said top surface to prevent an object inserted into said receptacle at an object angle that is substantially perpendicular to said top surface from passing entirely through said protective member, thereby preventing said object from contacting said receptacle when said object is disposed within said basin.

35. The apparatus of claim 34, wherein said protective member includes a plurality of feet depending from said protective member bottom surface to space said protective member from said receptacle and to enable said sterile medium to flow between said protective member and said receptacle.

36. The apparatus of claim 34, wherein said protective member includes a continuous periphery contoured to substantially match and fit along a periphery of at least one of a bottom wall of said basin and a side wall of said basin.

37. The apparatus of claim 34, wherein said receptacle includes a pouch to receive and secure said protective member to said receptacle.

38. The apparatus of claim 34, wherein said receptacle includes at least one fastener to secure said protective member to said receptacle.

39. The apparatus of claim 34, wherein said protective member is removably placed on said receptacle.

40. The apparatus of claim 34, wherein said protective member is integrally formed with said receptacle.

41. The apparatus of claim 34, wherein said receptacle includes one of a container, a drape, a liner and a cover to contain said sterile medium, and wherein said drape, liner and cover are for placement within, and conform to, said basin to form said receptacle.

42. The apparatus of claim 34, wherein:
said basin comprises:
a bottom surface and a top, receptacle-facing surface,
a heated portion directly heated by a heater disposed adjacent said basin bottom surface, and
a non-heated portion coincident with said heated portion falling outside a perimeter of said basin heater;
said receptacle contacts the heated and non-heated portions of said basin; and
at least a portion of said protective member contacts an area of said receptacle in contact with said basin heated portion.

43. The apparatus of claim 34, wherein said protective member is disposed directly onto said receptacle such that no space exists between said receptacle and said protective member bottom surface.

44. In a thermal treatment system including a basin to thermally treat a sterile medium contained therein and a receptacle being disposed within said basin to contain said sterile medium, wherein an object disposed in said basin is thermally treated by said sterile medium, a protective device disposed within said basin to protect said receptacle, said protective device comprising a protective member disposed on said receptacle, said protective member including:
a bottom surface that faces said basin and a top surface that faces away from said basin; and
a plurality of holes defined therein configured to permit said sterile medium to flow through said protective member and thermally treat said object, wherein each of said plurality of holes extend from said top surface to said bottom surface, wherein each hole of said plurality of holes extends through said protective member at a non-perpendicular angle relative to said top surface to prevent said object inserted into said receptacle at an object angle that is substantially perpendicular to said protective member top surface from passing entirely through said protective member, thereby preventing said object from contacting said receptacle when said object is disposed within said basin.

45. The apparatus of claim 44, wherein said protective member includes a plurality of feet depending from said protective member bottom surface to space said protective member from said receptacle and to enable said sterile medium to flow between said protective member and said receptacle.

46. The apparatus of claim 44, wherein said protective member includes a continuous periphery contoured to substantially match and fit along a periphery of at least one of a bottom wall of said basin and a side wall of said basin.

47. The apparatus of claim 44, wherein said receptacle includes a pouch to receive and secure said protective member to said receptacle.

48. The apparatus of claim 44, wherein said receptacle includes at least one fastener to secure said protective member to said receptacle.

49. The apparatus of claim 44, wherein said protective member is integrally formed with said receptacle.

50. The apparatus of claim 44, wherein said receptacle includes one of a container, a drape, a liner and a cover to contain said sterile medium, and wherein said drape, liner and cover are for placement within, and conform to, said basin to form said receptacle.

51. The apparatus of claim 44, wherein:
said basin comprises:
  a bottom surface and a top, receptacle-facing surface,
  a heated portion directly heated by a heater disposed adjacent said basin bottom surface, and
  a non-heated portion coincident with said heated portion falling outside a perimeter of said basin heater;
said receptacle contacts the heated and non-heated portions of said basin; and
at least a portion of said protective member contacts an area of said receptacle in contact with said basin heated portion.

52. A method of preventing puncture of a receptacle used to contain a sterile medium in a basin of a thermal treatment system, wherein an object disposed in said basin are thermally treated by said sterile medium, said method comprising:
  (a) re-enforcing at least a portion of said receptacle within said basin to be resistive to penetration with a protective member disposed on said receptacle, wherein said protective member includes:
    a bottom surface facing said basin and a top surface facing away from said basin, and
    a plurality of holes configured to permit said sterile medium to flow through said protective member and thermally treat said objects, wherein each hole of said plurality of holes extends from said top surface to said bottom surface, and wherein each hole of said plurality of holes extends through the protective member at a non-perpendicular angle relative to said top surface to prevent an object inserted into said receptacle at an object angle that is substantially perpendicular to said top surface from passing entirely through said protective member, thereby preventing said object from contacting said receptacle when said object is disposed within said basin; and
  (b) enabling said sterile medium to flow through said protective member and thermally treat said objects via the plurality of holes defined in said protective member.

53. The method of claim 52, wherein (a) further includes (a.1) removably placing said protective member on said receptacle.

54. The method of claim 52, wherein (a) further includes (a.1) securing said protective member to said receptacle via a pouch disposed on said receptacle.

55. The method of claim 52, wherein (a) further includes (a.1) securing said protective member to said receptacle via at least one fastener disposed on said receptacle.

* * * * *